United States Patent
Fairchild et al.

(10) Patent No.: US 11,041,208 B2
(45) Date of Patent: Jun. 22, 2021

(54) URINE BIOMARKERS FOR DETECTING GRAFT REJECTION

(71) Applicants: The Cleveland Clinic Foundation, Cleveland, OH (US); THE UAB RESEARCH FOUNDATION, Birmingham, AL (US)

(72) Inventors: Robert L. Fairchild, Mayfield Village, OH (US); Roslyn Bernstein Mannon, Birmingham, AL (US)

(73) Assignees: THE CLEVELAND CLINIC FOUNDATION, Cleveland, OH (US); THE UAB RESEARCH FOUNDATION, Birmingham, AL (US)

( * ) Notice: Subject to any disclaimer, the term of this patent is extended or adjusted under 35 U.S.C. 154(b) by 162 days.

(21) Appl. No.: 16/110,964

(22) Filed: Aug. 23, 2018

(65) Prior Publication Data

US 2019/0085397 A1 Mar. 21, 2019

Related U.S. Application Data

(63) Continuation-in-part of application No. 16/004,055, filed on Jun. 8, 2018, now abandoned.

(60) Provisional application No. 62/516,907, filed on Jun. 8, 2017.

(51) Int. Cl.
C12Q 1/68 (2018.01)
C12Q 1/6883 (2018.01)
C12Q 1/70 (2006.01)

(52) U.S. Cl.
CPC ........... *C12Q 1/6883* (2013.01); *C12Q 1/701* (2013.01); *C12Q 2600/158* (2013.01)

(58) Field of Classification Search
None
See application file for complete search history.

(56) References Cited

FOREIGN PATENT DOCUMENTS

WO WO 2013/173493 11/2013
WO WO 2015/200873 12/2015

OTHER PUBLICATIONS

Hricik et al., Adverse Outcomes of Tacrolimus Withdrawal in Immune-Quiescent Kidney Transplant Recipients. J Am Soc Nephrol. Dec. 2015;26(12):3114-22.
Hricik et al., Multicenter Validation of Urinary CXCL9 as a Risk-Stratifying Biomarker for Kidney Transplant Injury. Am J Transplant. Oct. 2013;13(10):2634-44.
Keslar et al., Detection of Shared and Distinct Gene Expression Signatures in Tissue and Urine During Acute Rejection of Kidney Grafts. Poster presented at American Translplant Congress, Apr. 29-May 2, 2017, Chicago, IL, 1 page.
Keslar et al., Multicenter Evaluation of a Standardized Protocol for Noninvasive Gene Expression Profiling. Am J Transplant. Jul. 2013;13(7):1891-7.
Keslar et al., NanoSTring Detection of Gene Signatures in Urine During Accute Cellular Rejection of Kidney Grafts. Poster presented at American Transplant Congress, Jun. 11-15, 2016, Boston, MA, 1 page.
Keslar et al., Unique Gene Expression Signatures in Urine Distinguish BK Virus Nephropathy from Acute Rejection in Kidney Transplant Patients with Graft Dysfunction. Poster presented at The Cleveland Clinic Foundation Research Day. Sep. 14, 2018, 1 page.
Merhi et al., Role for Urinary Biomarkers in Diagnosis of Acute Rejection in the Transplanted Kidney. World J Transplant. Dec. 24, 2014;5(4):251-60.
Muthukumar et al., Allograft Rejection and Tubulointerstitial Fibrosis in Human Kidney Allografts: Interrogation by Urinary Cell mRNA Profiling. Transplant Rev (Orlando). Jul. 2014;28(3):145-54.
Song et al., Genomic and Proteomic Fingerprints of Acute Rejection in Peripheral Blood and Urine. Transplant Rev (Orlando) . Apr. 2015;29(2):60-7.
Suthanthiran et al., Urinary-cell mRNA Profile and Acute Cellular Rejection in Kidney Allografts. N Engl J Med. Jul. 4, 2013;369(1):20-31.
Tatapudi et al., Noninvasive Detection of Renal Allograft Inflammation by Measurements of mRNA for IP-10 and CXCR3 in Urine. Kidney Int. Jun. 2004;65(6):2390-7.

*Primary Examiner* — Jehanne S Sitton
(74) *Attorney, Agent, or Firm* — Casimir Jones, S.C.; Jason R. Bond (57) ABSTRACT

Provided herein are compositions, systems, kits, and methods for detecting rejection, or an elevated risk of rejection, of an organ or tissue graft (e.g., kidney graft) in a subject by detecting one, or a panel of, RNA markers in a urine sample from the subject. In certain embodiments, kidney graft injury is detected by measuring one or more of the RNA markers disclosed herein. In some embodiments, the one or more markers are employed to distinguish between acute graft rejection and BK virus nephropathy.

8 Claims, 11 Drawing Sheets

URINE BIOMARKERS FOR DETECTING GRAFT REJECTION

The present application is a Continuation-in-part of U.S. application Ser. No. 16/004,055 filed Jun. 8, 2018, which claims priority to U.S. Provisional application 62/516,907 filed Jun. 8, 2017, both of which are herein incorporated by reference in their entireties as if fully set forth herein.

STATEMENT REGARDING GOVERNMENT FUNDING

This invention was made with government support under AI084150 and AI063594 awarded by the National Institutes of Health. The government has certain rights in the invention.

FIELD

Provided herein are compositions, systems, kits, and methods for detecting rejection, or an elevated risk of rejection, of an organ or tissue graft (e.g., kidney graft) in a subject by detecting one, or a panel of, RNA markers in a urine sample from the subject. In certain embodiments, kidney graft injury is detected by measuring one or more of the RNA markers disclosed herein. In some embodiments, the one or more markers are employed to distinguish between acute graft rejection and BK virus nephropathy.

BACKGROUND

Kidney disease and failure are common medical problems associated with many illnesses. One in three Americans is considered to be at risk for kidney disease. The predictors include age above 60, diabetes, high blood pressure, and family history of kidney disease. Kidney disease can be chronic (ongoing over years with slowly declining kidney function) or acute (sharp decline in kidney function, either nearly immediate or within months). When kidney function declines to a level of reduced effectiveness, this leaves the patient with only 10-15% of kidney function remaining, giving a diagnosis of kidney failure to the patient. Common treatments for kidney failure include dialysis and kidney transplants. In 2014, about 17,000 kidney transplants occurred in the US. Of these, 11,570 kidneys came from deceased donors and 5,537 came from living donors. Typically, within the first year of a kidney transplant, there is a 7% failure rate, and within 10 years of a transplant, there is a 45% failure rate. In addition, kidney supply is not fulfilling kidney demand leading to patient death due to not receiving a transplant in time. In 2014, nearly 5,000 patients died while waiting for a transplant, on a waiting list, and more than 3,600 became too sick to receive a transplant.

Transplanted kidneys fail for various reasons, including kidney rejection. Rejection can be acute, very soon after surgery, and it occurs in about 15% of cases. There is also chronic rejection, which takes place over longer periods of time, generally taking years. Most patients who experience kidney rejection do not lose the transplanted kidney but instead go on to other treatments to manage the immune system's rejection. Accurate, early detection of the rejection can lead to better early intervention and treatment of patients. In addition, successful transplants are less expensive than dialysis, in most cases, and lead patients to live longer, healthier lives. Each year one in five transplants is performed into a patient who had previously received a transplant and is either suffering from kidney failure or kidney transplant rejection. For patients that experience transplant rejection and are unable to get another organ, they receive dialysis at a cost of $70,000 per year in the US.

Effective monitoring of kidney transplant patients for rejection is a continuing problem. As of 2016, the most effective methods of testing for transplanted kidney failure are generally considered to be through a combination of monitoring non-specific byproducts of kidney rejection, such as creatinine levels. Physicians further make a clinical assessment of a variety of patient symptoms commonly associated with kidney transplant rejection, including flu-like symptoms, chills, body aches, nausea, cough, shortness of breath, and a general sense of unease, 10 followed by or in concert with a biopsy of the kidney. Kidney biopsies are not considered a viable option for continuous, regular monitoring, and efforts to determine kidney rejection through less invasive means, including blood and urine testing, are continuously increasing. Although there have been various blood and urine tests developed during the last several years, as of March 2016, there does not seem to be a test that has been adopted for widespread clinical use. This is in part because kidney rejection is believed to be a heterologous process with many causes, depending on compatibility of the donor and recipient, and other reasons as well. As a result, some in the medical community do not believe a uniform, accurate test is possible. Monitoring of the different byproducts of kidney disease, such as serum creatinine antibodies in the blood have been attempted through blood and urine tests, but none appears to have been generally adopted as a new gold standard by the medical community. None in use so far has been established to detect kidney rejection across all types of transplant patients. A combination of creatinine monitoring and biopsy is a frequently used approach in medical environments. Acute cellular rejection is a significant type of kidney organ rejection that requires further treatment to the patient to compensate for rejection, or, at times, removal of the rejected kidney.

SUMMARY

Provided herein are compositions, systems, kits, and methods for detecting rejection, or an elevated risk of rejection, of an organ or tissue graft (e.g., kidney graft) in a subject by detecting one, or a panel, of RNA markers in a urine sample from the subject. In certain embodiments, kidney graft injury is detected by measuring one or more of the RNA markers disclosed herein. In some embodiments, the one or more markers are employed to distinguish between acute graft rejection and BK virus nephropathy.

In some embodiments, provided herein are methods for detecting rejection, or an elevated risk of rejection, or an organ or tissue graft in a subject comprising: detecting an upregulated level of at least one first RNA marker (e.g., 1 . . . 10 . . . 25 . . . 35) in a sample from a subject and/or a downregulated level of at least one second RNA marker (e.g., 1 . . . 10 . . . 25 . . . 35) in said sample from said subject, and thereby detecting acute rejection and/or elevated risk of rejection of said organ or tissue graft or detecting kidney graft injury, or distinguishing between acute graft rejection and BK virus nephropathy, wherein said sample comprises urine (or other sample type, such as serum or plasma) from said subject, wherein said subject has a tissue or organ graft, wherein said at least one first RNA marker that is detected as being upregulated is selected from the group consisting of: CXCL10, CXCL9, CXCL11, PRF1, CCL5, CX3CL1, IDO1, GZMA, LAG3, CD3D, CD27, KLRK1, GZMK, MMPI, CD8A, GZMB, ETS1, CXCR6, CCL2, IL2RB, CTLA4, MSR1, FYN, ITGA6, CD3E, LCK, CD2, IRF8, CD3G, CD247, GZMH, ITK, CD38, CDK1, ZAP70, LIF, CD7, CD40, CD6, IL21R, SIGIRR, CDH1, CD81, CD74, STAT1, AXL, TBX21, COG7, TCRA, C1QB, NKG7, THBS1, C1QA, EPCAM, DPP4, HLA-DPA1, TIGIT, HLA-DPB1, CXCL13, C1R, CD5, GPR171, EFEMP1, HLA-DMA, LY9, CCL8, CD96, HAVCR2, NFATC2, LAMC2, IFNG, STAT4, APOE, C4B, CTSL, SOCS1, PVR, CCR5, CD86, TNFSF12, SIGLEC1, ST6GAL1, C3, KLRC2, CTSW, CARD11, GNLY, PSMB10, ICOS, TAP1, TNFRSF11B, ITGA1, IRF4, CD4, CD84, CSF1, SH2D1A, CD8B, CD47, ABCB1, SLAMF1, HLA-DMB, IFI35, A2M, HLA-DRA, C1QBP, SPP1, VCAM1, NELL2, FLT3LG, ITGA4, TNFRSF10B, RUNX3, SERPING1, KLRC1, NLRC5, HPRT1, IKBKE, TNF, ADA PDCD1, C1S, CCR2, TAB1, IL12RB1, IL2RA, PSEN2, LRP1, NOL7, SPN, TCF7, MFGE8, MST1R, IL10, LRRN3, PSMB9, PPIA, AGK, EDC3, CD80, PSMB8, CD276, BIRC5, TNFRSF9, TP53, ZC3H14, HLA-DRB3, ICOSLG, CD200, PIN1, EGR2, ITGAE, TRAF2, ABL1, ALCAM, IRF5, SF3A3, HRAS, NOD1, PDCD1LG2, IL16, LILRB1, and IRF3, and wherein said at least one second RNA marker that is detected as being downregulated is selected from the group consisting of: ANXA1, BASP1, BCL6, BLK, CAMP, CCL17, CCL22, CCR3, CEACAM1, CEACAM6, CFD, CR2, CSF2RB, CSF3R, CXCL1, CXCL6, CXCR1, CXCR2, FUT7, IFNL1, IL18RAP, IL19, IL1A, IL1RAP, IL1RN, IL8, ITGAX, LCN2, LILRB3, LYN, MAPK3, MEFV, MYD88, OSM, PBEF1, POLR2A, PRKCD, PTGS2, S100A12, S100A7, S100A8, SH2B2, SH2D1B, SPINK5, TFE3, TLR1, TNFRSF10C, TNFRSF11A, TNFRSF1A, TNFSF14, ADAMS, ARG2, BCL10, CASP3, CD46, CFI, DMBT1, DOCK9, DUSP4, IF127, IKBKB, IL23A, ISG15, ITCH, LGALS3, MAPK8, MUC1, NOS2A, SERPINA3, SERPINB2, SYT17, and TREM1.

In certain embodiments, the subject, at the time the sample was obtained, is taking a first immunosuppressant. In particular embodiments, the method further comprises the step of performing at least one of the following: i) treating said subject with a second immunosuppressant that is different from said first immunosuppressant; ii) generating and/or transmitting a report that indicates said at least one first RNA maker is upregulated and/or said at least one second RNA marker is downregulated in said sample, and that said subject is in need of an immunosuppressant different from said first immunosuppressant and/or is in need of a having said tissue and/or organ graft removed (and/or in need of having said tissue or graft replaced with a different tissue or graft); iii) generating and/or transmitting a report that indicates said at least one first RNA maker is upregulated and/or said at least one second RNA marker is downregulated in said sample, and that said subject has acute rejection and/or elevated risk of rejection of said organ or tissue graft; and iv) characterizing said subject as having acute rejection and/or an elevated risk of rejection of said organ or tissue graft, based on finding that said at least one first RNA maker is upregulated and/or said at least one second RNA marker is downregulated in said sample.

In particular embodiments, the organ or tissue graft comprises a kidney or kidney tissue graft. In further embodiments, the subject at the time of collection of said sample was being treated with, and/or wherein said sample comprises, an immunosuppressant protein that comprises an extracellular domain of CTLA-4. In further embodiments, the immunosuppressant protein further comprises an Fc region. In other embodiments, the immunosuppressant protein comprises Belatacept or Abatacept. In other embodiments, the detecting at least one of said first and/or said at least one second RNA marker comprises detecting at least two (e.g., 2 . . . 5 . . . 10 . . . 15 . . . 20 . . . 25) of said first and/or second RNA markers. In certain embodiments, the methods further comprise detecting an additional marker selected from upregulated TGFB1 and/or upregulated HLA.A. In other embodiments, the methods further comprise detecting an additional marker selected from upregulated CXCL9 and/or upregulated CXCL10. In other embodiments, the methods further comprise detecting all of the following: i) upregulated CXCL11, TGFB1, LIF, CCL5, TNF, HLA.A, and ETS1, and ii) downregulated IL19, CCL17, and IFIT1.

In certain embodiments, the provided herein are kits, compositions, and systems comprising: a) a sample from a subject having a tissue or organ graft, wherein said sample comprises urine (or other sample type, such as serum, plasma, whole blood, etc.) from said subject; and b) reagents (e.g., sequencing reagents, nucleic acid probes, RT enzymes, polymerases, detectable labels, expression panels, NANOSTRINGS reagents, etc.) configured for detecting the level of at least one RNA marker selected from the group consisting of: CXCL10, CXCL9, CXCL11, PRF1, CCL5, CX3CL1, IDO1, GZMA, LAG3, CD3D, CD27, KLRK1, GZMK, MMPI, CD8A, GZMB, ETS1, CXCR6, CCL2, IL2RB, CTLA4, MSR1, FYN, ITGA6, CD3E, LCK, CD2, IRF8, CD3G, CD247, GZMH, ITK, CD38, CDK1, ZAP70, LIF, CD7, CD40, CD6, IL21R, SIGIRR, CDH1, CD81, CD74, STAT1, AXL, TBX21, COG7, TCRA, C1QB, NKG7, THBS1, C1QA, EPCAM, DPP4, HLA-DPA1, TIGIT, HLA-DPB1, CXCL13, C1R, CD5, GPR171, EFEMP1, HLA-DMA, LY9, CCL8, CD96, HAVCR2, NFATC2, LAMC2, IFNG, STAT4, APOE, C4B, CTSL, SOCS1, PVR, CCR5, CD86, TNFSF12, SIGLEC1, ST6GAL1, C3, KLRC2, CTSW, CARD11, GNLY, PSMB10, ICOS, TAP1, TNFRSF11B, ITGA1, IRF4, CD4, CD84, CSF1, SH2D1A, CD8B, CD47, ABCB1, SLAMF1, HLA-DMB, IFI35, A2M, HLA-DRA, C1QBP, SPP1, VCAM1, NELL2, FLT3LG, ITGA4, TNFRSF10B, RUNX3, SERPING1, KLRC1, NLRC5, HPRT1, IKBKE, TNF, ADA PDCD1, C1S, CCR2, TAB1, IL12RB1, IL2RA, PSEN2, LRP1, NOL7, SPN, TCF7, MFGE8, MST1R, IL10, LRRN3, PSMB9, PPIA, AGK, EDC3, CD80, PSMB8, CD276, BIRC5, TNFRSF9, TP53, ZC3H14, HLA-DRB3, ICOSLG, CD200, PIN1, EGR2, ITGAE, TRAF2, ABL1, ALCAM, IRF5, SF3A3, HRAS, NOD1, PDCD1LG2, IRF3, ANXA1, BASP1, BCL6, BLK, CAMP, CCL17, CCL22, CCR3, CEACAM1, CEACAM6, CFD, CR2, CSF2RB, CSF3R, CXCL1, CXCL6, CXCR1, CXCR2, FUT7, IFNL1, IL18RAP, IL19, IL1A, IL1RAP, IL1RN, IL8, ITGAX, LCN2, LILRB3, LYN, MAPK3, MEFV, MYD88, OSM, PBEF1, POLR2A, PRKCD, PTGS2, S100A12, S100A7, S100A8, SH2B2, SH2D1B, SPINK5, TFE3, TLR1, TNFRSF10C, TNFRSF11A, TNFRSF1A, TNFSF14, ADAMS, ARG2, BCL10, CASP3, CD46, CFI, DMBT1, DOCKS, DUSP4, IFI27, IKBKB, IL23A, ISG15, ITCH, LGALS3, MAPK8, MUC1, NOS2A, SERPINA3, SERPINB2, SYT17, IL16, LILRB1, and TREM1.

In some embodiments, provided herein are kits, compositions, and systems comprising: a) a sample from a subject having a tissue or organ graft, wherein said sample comprises urine (or other sample type, such as serum, plasma, whole blood, etc.) from said subject; and b) reagents (e.g., sequencing reagents, nucleic acid probes, RT enzymes, polymerases, detectable labels, expression panels, NANOSTRINGS reagents, etc.) configured for detecting the level of at least one RNA marker selected from the group consisting of: CXCL11, TGFB1, LIF, CCL5, TNF, HLA.A, and ETS1, IL19, CCL17, and IFIT1.

In some embodiments, said urine sample is from a subject having a kidney tissue or organ graft. In certain embodiments, the subject at the time of collection of said sample was being treated with, and/or wherein said sample comprises, an immunosuppressant protein that comprises an extracellular domain of CTLA-4. In further embodiments, the immunosuppressant protein further comprises an Fc region. In additional embodiments, the immunosuppressant protein comprises Belatacept or Abatacept.

In some embodiments, provided herein are methods of detecting rejection, or an elevated risk of rejection, of an organ or tissue graft, or detecting kidney graft injury, or distinguishing between acute graft rejection and BK virus nephropathy, in a subject comprising: detecting an upregulated level of at least one first RNA marker (e.g., 1 . . . 10 . . . 25 . . . 35) in a sample from a subject and/or a downregulated level of at least one second RNA marker (e.g., 1 . . . 10 . . . 25 . . . 35) in said sample from said subject, and thereby detecting acute rejection and/or elevated risk of rejection of said organ or tissue graft, wherein said sample comprises urine (or other sample, such as blood, plasma, whole blood, or tissue biopsy) from said subject, wherein said subject has a tissue or organ graft, wherein said at least one first RNA marker that is detected as being upregulated is selected from the group consisting of: TNFRSF11B, ETS1, CXCL10, CDK1, CXCL9, SIGIRR, CD274, CXCL11, ITGA6, and SF3A3, and wherein said at least one second RNA marker that is detected as being downregulated, are selected from the group consisting of: TNFSF4, ATG16L1, MERTK, DHX16, CXCL14, IL19, CCL17, ATF1, CFD, IFIT1, CD163, ELK1, DPP4, and LAMP2. In certain embodiments, the methods further comprise detecting an additional marker selected from upregulated CXCL9 and/or upregulated CXCL10.

In particular embodiments, the subject was taking a first immunosuppressant at the time said sample was obtained. In further embodiments, the methods further comprise the step of performing at least one of the following: i) treating said subject with a second immunosuppressant that is different from said first immunosuppressant; ii) generating and/or transmitting a report that indicates said at least one first RNA maker is upregulated and/or said at least one second RNA marker is downregulated in said sample, and/or that said subject is in need of an immunosuppressant different from said first immunosuppressant, and/or is in need of a having said tissue and/or organ graft removed or replaced; iii) generating and/or transmitting a report that indicates said at least one first RNA maker is upregulated and/or said at least one second RNA marker is downregulated in said sample, and/or that said subject has acute rejection and/or elevated risk of rejection of said organ or tissue graft; and iv) characterizing said subject as having acute rejection and/or an elevated risk of rejection of said organ or tissue graft, based on finding that said at least one first RNA maker is upregulated and/or said at least one second RNA marker is downregulated in said sample.

In certain embodiments, said organ or tissue graft comprises a kidney or kidney tissue graft. In further embodiments, the subject has been treated with an anti-CD52 monoclonal antibody or antigen binding fragment thereof. In additional embodiments, the anti-CD52 monoclonal antibody comprises Alemtuzumab/CAMPATH. In some embodiments, the subject at the time of collection of said sample was being treated with, and/or wherein said sample comprises, an immunosuppressant comprising tacrolimus (aka FK506). In some embodiments, the at least one of said first and/or second RNA marker comprises detecting at least two (e.g., 2 . . . 5 . . . 10 . . . 15 . . . 25 . . . 35) of said first and/or second RNA markers. In other embodiments, the detecting at least one of said first and/or second RNA marker comprises detecting at least four of said first and/or second RNA markers.

In some embodiments, provided herein are compositions, kits, or systems comprising: a) a sample from a subject having a tissue or organ graft, wherein said sample comprises urine from said subject; and b) reagent configured for detecting the level of at least one RNA marker selected from the group consisting of: CCL17, CD163, CD274, CDK1, CFD, CXCL10, CXCL11, CXCL14, CXCL9, DHX16, DPP4, ELK1, ETS1, IFIT1, IL19, ITGA6, LAMP2, MERTK, SF3A3, SIGIRR, TNFRSF11B, and TNFSF4.

In certain embodiments, the urine sample is from a subject having a kidney tissue or organ graft. In further embodiments, the subject has been treated with an anti-CD52 monoclonal antibody or antigen binding fragment thereof for immunosuppression of said tissue or graft. In other embodiments, the anti-CD52 monoclonal antibody comprises Alemtuzumab/CAMPATH. In other embodiments, the subject at the time of collection of said sample was being treated with, and/or wherein said sample comprises, an immunosuppressant comprising tacrolimus (aka FK506).

In some embodiments, provided herein are methods of detecting rejection or BK virus infection (e.g., distinguishing between acute rejection and BK virus infection), or an elevated risk of rejection, of an organ or tissue graft in a subject comprising: detecting an upregulated level of at least one first RNA marker in a sample from a subject and/or a downregulated level of at least one second RNA marker in said sample from said subject, and thereby detecting acute rejection and/or elevated risk of rejection of said organ or tissue graft, wherein said sample comprises urine from said subject, wherein said subject has a tissue or organ graft, wherein said at least one first RNA marker that is detected as being upregulated and is selected from the group consisting of: SIGLEC1, CD163, PSEN1, DPP4, CEACAM8, PYCARD, MTMR14, ICOSLG, NOL7, C2, HLA.DRB3, CD68, ST6GAL1, SLAMF1, MERTK, PRAME, ELK1, STAT4, CD99, CD86, LAMP2, ITGB1, IL21R, IL6ST, TNF, GPATCH3, GPI, ATF1, PIN1, and YTHDF2, and wherein said at least one second RNA marker that is detected as being downregulated, is selected from the group consisting of: HMGB1, MAPK9, SPA17, TNFRSF11B, GTF3C1, BST2, PRPF38A, MAF, BATF, EGFR, CD274, CCL17, SERPINA3, GBP1, and PBEF1. In some embodiments, the methods further comprise detecting an additional marker selected from the group consisting of: C1QBP, CD6, CXCL6, LIF, and AXL. In other embodiments, the methods further comprise detecting an additional marker selected from the group consisting of: CREBBP, PSMB7, NFATC1, TGFB1, and FCER1G. In other embodiments, the detecting comprise detecting all of the following: SIGLEC1, CD163, PSEN1, DPP4, CEACAM8, PYCARD, MTMR14, ICOSLG, NOL7, C2, HLA.DRB3, CD68, ST6GAL1, SLAMF1, MERTK, PRAME, ELK1, STAT4, CD99, CD86, LAMP2, ITGB1, IL21R, IL6ST, TNF, GPATCH3, GPI, ATF1, PIN1, YTHDF2, HMGB1, MAPK9, SPA17, TNFRSF11B, GTF3C1, BST2, PRPF38A, MAF, BATF, EGFR, CD274, CCL17, SERPINA3, GBP1, PBEF1, C1QBP, CD6, CXCL6, LIF, AXL, CREBBP, PSMB7, NFATC1, TGFB1, and FCER1G.

In certain embodiments, the BK virus infection is detected (and distinguished from acute rejection). In other embodiments, acute rejection is detected (e.g., and distinguished from BK virus infection). In some embodiments, the organ or tissue graft comprises a kidney or kidney tissue graft. In additional embodiments, the subject has been treated with an anti-CD52 monoclonal antibody or antigen binding fragment thereof. In some embodiments, the anti-CD52 monoclonal antibody comprises Alemtuzumab/CAMPATH. In certain embodiments, said subject at the time of collection of said sample was being treated with, and/or wherein said sample comprises, an immunosuppressant comprising tacrolimus (aka FK506).

In some embodiments, provided herein are kits, compositions, and systems comprising: a) a sample from a subject having a tissue or organ graft, wherein said sample comprises urine from said subject; and b) reagent configured for detecting the level of at least one RNA marker selected from the group consisting of: ATF1, BATF, BST2, C2, CCL17, CD163, CD274, CD68, CD86, CD99, CEACAM8, DPP4, EGFR, ELK1, GBP1, GPATCH3, GPI, GTF3C1, HLA.DRB3, HMGB1, ICOSLG, IL21R, IL6ST, ITGB1, LAMP2, MAF, MAPK9, MERTK, MTMR14, NOL7, PBEF1, PIN1, PRAME, PRPF38A, PSEN1, PYCARD, SERPINA3, SIGLEC1, SLAMF1, SPA17, ST6GAL1, STAT4, TNF, TNFRSF11B, and YTHDF2.

In some embodiments, provided herein are kits, compositions, and systems comprising: a) a sample from a subject having a tissue or organ graft, wherein said sample comprises urine from said subject; and b) reagents configured for detecting the level of at least one (e.g., 1 . . . 10 . . . 25 . . . 35 . . . 45 . . . or more) RNA marker selected from the group consisting of: SIGLEC1, CD163, PSEN1, DPP4, CEACAM8, PYCARD, MTMR14, ICOSLG, NOL7, C2, HLA.DRB3, CD68, ST6GAL1, SLAMF1, MERTK, PRAME, ELK1, STAT4, CD99, CD86, LAMP2, ITGB1, IL21R, IL6ST, TNF, GPATCH3, GPI, ATF1, PIN1, YTHDF2, HMGB1, MAPK9, SPA17, TNFRSF11B, GTF3C1, BST2, PRPF38A, MAF, BATF, EGFR, CD274, CCL17, SERPINA3, GBP1, PBEF1, C1QBP, CD6, CXCL6, LIF, AXL, CREBBP, PSMB7, NFATC1, TGFB1, and FCER1G.

In certain embodiments, the urine sample is from a subject having a kidney tissue or organ graft. In further embodiments, the subject has been treated with an anti-CD52 monoclonal antibody or antigen binding fragment thereof. In additional embodiments, the anti-CD52 monoclonal antibody comprises Alemtuzumab/CAMPATH. In some embodiments, the subject at the time of collection of said sample was being treated with, and/or wherein said sample comprises, an immunosuppressant comprising tacrolimus (aka FK506).

In some embodiments, provided herein are methods of detecting rejection, or an elevated risk of rejection, or an organ or tissue graft in a subject comprising: detecting an upregulated level of at least one first RNA marker (e.g., mRNA sequence or portion thereof) in a sample from a subject and/or a downregulated level of at least one second RNA marker (e.g., mRNA sequence or portion thereof) in the sample from the subject, and thereby detecting acute rejection and/or elevated risk of rejection of the organ or tissue graft, wherein the sample comprises urine from the subject, wherein the subject has a tissue or organ graft, wherein the first RNA marker (e.g., mRNA sequence or portion thereof) that is detected as being upregulated is selected from the group consisting of: CXCL10, CXCL9, CXCL11, PRF1, CCL5, CX3CL1, IDO1, GZMA, LAG3, CD3D, CD27, KLRK1, GZMK, MMPI, CD8A, GZMB, ETS1, CXCR6, CCL2, IL2RB, CTLA4, MSR1, FYN, ITGA6, CD3E, LCK, CD2, IRF8, CD3G, CD247, GZMH, ITK, CD38, CDK1, ZAP70, LIF, CD7, CD40, CD6, IL21R, SIGIRR, CDH1, CD81, CD74, STAT1, AXL, TBX21, COG7, TCRA, C1QB, NKG7, THBS1, C1QA, EPCAM, DPP4, HLA-DPA1, TIGIT, HLA-DPB1, CXCL13, C1R, CD5, GPR171, EFEMP1, HLA-DMA, LY9, CCL8, CD96, HAVCR2, NFATC2, LAMC2, IFNG, STAT4, APOE, C4B, CTSL, SOCS1, PVR, CCR5, CD86, TNFSF12, SIGLEC1, ST6GAL1, C3, KLRC2, CTSW, CARD11, GNLY, PSMB10, ICOS, TAP1, TNFRSF11B, ITGA1, IRF4, CD4, CD84, CSF1, SH2D1A, CD8B, CD47, ABCB1, SLAMF1, HLA-DMB, IFI35, A2M, HLA-DRA, C1QBP, SPP1, VCAM1, NELL2, FLT3LG, ITGA4, TNFRSF10B, RUNX3, SERPING1, KLRC1, NLRC5, HPRT1, IKBKE, TNF, ADA, PDCD1, C1S, CCR2, TAB1, IL12RB1, IL2RA, PSEN2, LRP1, NOL7, SPN, TCF7, MFGE8, MST1R, IL10, LRRN3, PSMB9, PPIA, AGK, EDC3, CD80, PSMB8, CD276, BIRC5, TNFRSF9, TP53, ZC3H14, HLA-DRB3, ICOSLG, CD200, PIN1, EGR2, ITGAE, TRAF2, ABL1, ALCAM, IRF5, SF3A3, HRAS, NOD1, PDCD1LG2, and IRF3; and wherein the second RNA marker (e.g., mRNA sequence or portion thereof) that is detected as being downregulated is selected from the group consisting of: ANXA1, BASP1, BCL6, BLK, CAMP, CCL17, CCL22, CCR3, CEACAM1, CEACAM6, CFD, CR2, CSF2RB, CSF3R, CXCL1, CXCL6, CXCR1, CXCR2, FUT7, IFNL1, IL18RAP, IL19, IL1A, IL1RAP, IL1RN, IL8, ITGAX, LCN2, LILRB3, LYN, MAPK3, MEFV, MYD88, OSM, PBEF1, POLR2A, PRKCD, PTGS2, S100A12, S100A7, S100A8, SH2B2, SH2D1B, SPINK5, TFE3, TLR1, TNFRSF10C, TNFRSF11A, TNFRSF1A, TNFSF14, and TREM1.

In particular embodiments, provided herein are methods of detecting rejection, or an elevated risk of rejection, or an organ or tissue graft, or detecting kidney graft injury, or distinguishing between acute graft rejection and BK virus nephropathy, in a subject comprising: detecting an upregulated level of at least one RNA marker in a sample from a subject, and thereby detecting acute rejection and/or elevated risk of rejection of the organ or tissue graft, wherein the sample comprises urine from the subject, wherein the subject has a tissue or organ graft, wherein the RNA marker that is detected as being upregulated is selected from the group consisting of: CXCL9, CXCL10, CXCL11, LAG3, CD38, CD3D, IDO1, CCL5, PRF1, KLRK1, TCRA, CTLA4, CD8A, STAT4, and CD27.

In certain embodiments, provided herein are methods of detecting rejection, or an elevated risk of rejection, or an organ or tissue graft in a subject comprising: detecting an upregulated level of at least one RNA marker in a sample from a subject, and thereby detecting acute rejection and/or elevated risk of rejection of the organ or tissue graft, wherein the sample comprises urine from the subject, wherein the subject has a tissue or organ graft, wherein the RNA marker that is detected as being upregulated is selected from the group consisting of: C1QA, C1QB, C1R, CD3E, CTSL, CX3CL1, GSMA, HAVCR2, IF135, MSR1, SIGLEC1, and ENG.

In some embodiments, the organ or tissue graft comprises a kidney or kidney tissue graft or a liver or liver tissue. In particular embodiments, the detecting at least one of the first and/or second RNA marker comprises detecting at least two, three, four, five, six, seven, . . . twenty . . . thirty . . . forty . . . or seventy-five of the first and/or second RNA markers. In certain embodiments, a Nanostrings assay is employed to detect the first and/or second RNA markers.

In particular embodiments, provided herein are kits, systems, and/or compositions comprising: a) a sample from a subject having a tissue or organ graft, wherein the sample comprises urine from the subject; and b) reagent configured for detecting the level of at least one RNA marker (e.g., mRNA sequence or portion thereof) selected from the group consisting of: CXCL10, CXCL9, CXCL11, PRF1, CCL5, CX3CL1, IDO1, GZMA, LAG3, CD3D, CD27, KLRK1, GZMK, MMPI, CD8A, GZMB, ETS1, CXCR6, CCL2, IL2RB, CTLA4, MSR1, FYN, ITGA6, CD3E, LCK, CD2, IRF8, CD3G, CD247, GZMH, ITK, CD38, CDK1, ZAP70, LIF, CD7, CD40, CD6, IL21R, SIGIRR, CDH1, CD81, CD74, STAT1, AXL, TBX21, COG7, TCRA, C1QB, NKG7, THBS1, C1QA, EPCAM, DPP4, HLA-DPA1, TIGIT, HLA-DPB1, CXCL13, C1R, CD5, GPR171, EFEMP1, HLA-DMA, LY9, CCL8, CD96, HAVCR2, NFATC2, LAMC2, IFNG, STAT4, APOE, C4B, CTSL, SOCS1, PVR, CCR5, CD86, TNFSF12, SIGLEC1, ST6GAL1, C3, KLRC2, CTSW, CARD11, GNLY, PSMB10, ICOS, TAP1, TNFRSF11B, ITGA1, IRF4, CD4, CD84, CSF1, SH2D1A, CD8B, CD47, ABCB1, SLAMF1, HLA-DMB, IF135, A2M, HLA-DRA, C1QBP, SPP1, VCAM1, NELL2, FLT3LG, ITGA4, TNFRSF10B, RUNX3, SERPING1, KLRC1, NLRC5, HPRT1, IKBKE, TNF, ADA, PDCD1, C1S, CCR2, TAB1, IL12RB1, IL2RA, PSEN2, LRP1, NOL7, SPN, TCF7, MFGE8, MST1R, IL10, LRRN3, PSMB9, PPIA, AGK, EDC3, CD80, PSMB8, CD276, BIRC5, TNFRSF9, TP53, ZC3H14, HLA-DRB3, ICOSLG, CD200, PIN1, EGR2, ITGAE, TRAF2, ABL1, ALCAM, IRF5, SF3A3, HRAS, NOD1, PDCD1LG2, IRF3, ANXA1, BASP1, BCL6, BLK, CAMP, CCL17, CCL22, CCR3, CEACAM1, CEACAM6, CFD, CR2, CSF2RB, CSF3R, CXCL1, CXCL6, CXCR1, CXCR2, FUT7, IFNL1, IL18RAP, IL19, IL1A, IL1RAP, IL1RN, IL8, ITGAX, LCN2, LILRB3, LYN, MAPK3, MEFV, MYD88, OSM, PBEF1, POLR2A, PRKCD, PTGS2, S100A12, S100A7, S100A8, SH2B2, SH2D1B, SPINK5, TFE3, TLR1, TNFRSF10C, TNFRSF11A, TNFRSF1A, TNFSF14, and TREM1.

In certain embodiments, provided herein are kits, systems, and/or compositions comprising: a) a sample from a subject having a tissue or organ graft, wherein the sample comprises urine from the subject; and b) reagent configured for detecting the level of at least one RNA marker selected from the group consisting of: C1QA, C1QB, C1R, CD3E, CTSL, CX3CL1, GSMA, HAVCR2, IF135, MSR1, SIGLEC1, and ENG.

In particular embodiments, provided herein are kits, systems, and/or compositions comprising: a) a sample from a subject having a tissue or organ graft, wherein the sample comprises urine from the subject; and b) reagent configured for detecting the level of at least one RNA marker selected from the group consisting of: CXCL9, CXCL10, CXCL11, LAG3, CD38, CD3D, IDO1, CCL5, PRF1, KLRK1, TCRA, CTLA4, CD8A, STAT4, and CD27. In certain embodiments, the urine sample is from a subject having a kidney tissue or organ graft.

DESCRIPTION OF THE FIGURES

FIG. 1 shows 49 genes that are upregulated by 5-fold or more in urine sediment of kidney transplant patients collected at the time of acute rejection (n=7) when compared to urine sediment collected from transplant recipients without rejection (n=14).

FIGS. 4A-4C show gene expression in graft tissue at the time of acute rejection in 9 subjects with acute rejection and 3 controls. One hundred fifty nine genes were upregulated but at least 5-fold in rejecting grafts when compared with controls.

FIG. 8 Panel B shows a 55 gene signature that distinguishes injury due to acute rejection from injury caused by BK virus nephropathy. In urine RNA samples that have been classified as "injured" using the 24 gene signature, the expression levels of these genes can identify the cause of the injury with an area under the curve of 0.962.

DETAILED DESCRIPTION

Provided herein are compositions, systems, kits, and methods for detecting rejection, or an elevated risk of rejection, of an organ or tissue graft (e.g., kidney graft) in a subject by detecting one, or a panel of, RNA markers in a urine sample from the subject. In certain embodiments, kidney graft injury is detected by measuring one or more of the RNA markers disclosed herein. In some embodiments, the one or more markers are employed to distinguish between acute graft rejection and BK virus nephropathy.

In certain embodiments, the nanostring detection platform (NanoString Technologies) is employed to detect mRNA markers in a sample. The nanostring platform technology uses molecular "barcodes" and single molecule imaging to detect and count hundreds of unique transcripts in a single reaction. The resulting tests are able to identify genetic sequences at much smaller quantities and without the need for extensive amplification of any genetic or proteomic material, which saves time and money. This process has been demonstrated to yield highly accurate results.

Example 1

The NanoString nCounter platform was used to interrogate increases, as well as decreases, in urine RNA targets to detect kidney graft injury. The NanoString nCounter technology allows multiplex detection of up to 800 gene targets in a single reaction/assay; high sensitivity vs. the use of microarray technology, high precision, and tolerance for RNA samples that have been partially degraded such as those in formalin-fixed/paraffin embedded tissue sections and urine. It is also very quick and the assays can be performed very cheaply.

Results

In initial analyses, we utilized urine samples collected from kidney transplant patients enrolled in the CTOT-16 study; 14 from control patients and 7 from patients with acute rejection that were interrogated by the NanoString platform. The gene expression analyses indicated that 102 genes are upregulated by at least 2-fold during ongoing rejection with 49 of those upregulated by at least 5-fold (FIG. 1). These genes included those that had previously been identified in the urine by qPCR (Table 1), supporting the utility of the NanoString platform to quantify gene expression in urine RNA samples from kidney transplant patients.

TABLE 1

| Gene | Fold-Change |
| --- | --- |
| CXCL10 | 25.6 |
| CXCL9 | 13.9 |
| Perforin | 7.8 |
| Interferon-γ | 4.3 |
| CD3E | 4.3 |
| Granzyme B | 3.5 |
| CXCR3 | 3.0 |
| OX40 | 2.7 |
| PD-1 | 2.6 |
| FOXP3 | 2.3 |
| OX40L | 2.3 |
| Granulysin | 2.3 |
| TLR4 | 2.1 |

Figure 2:
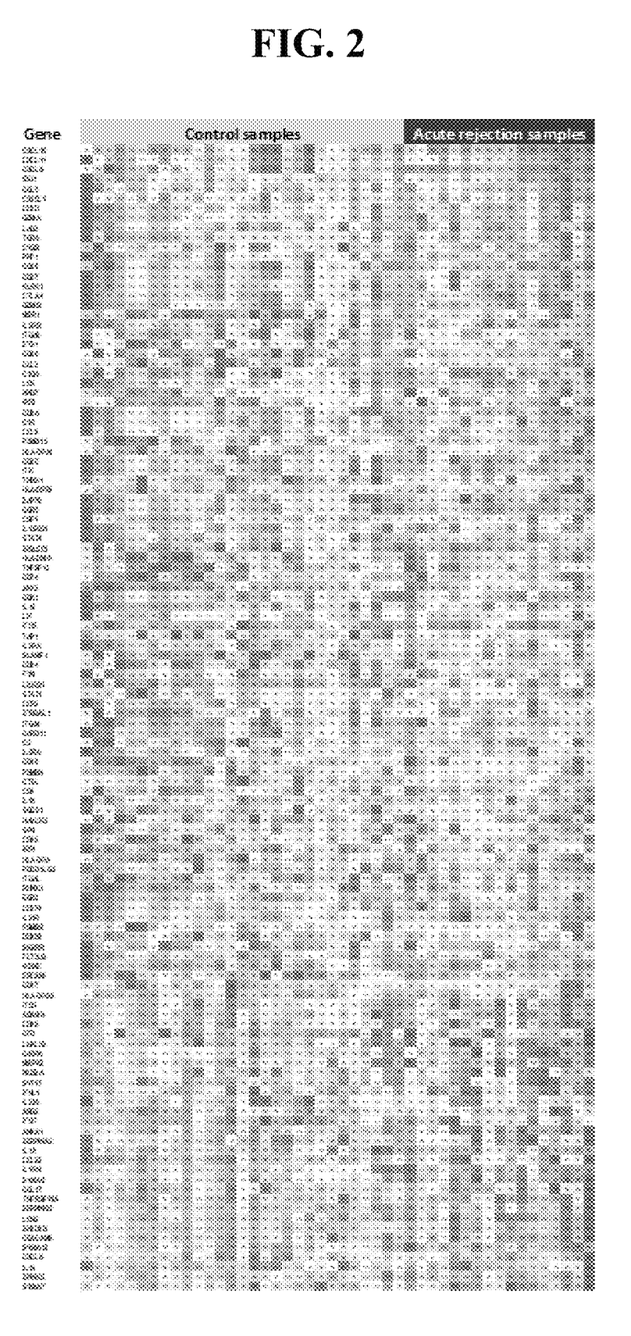
FIG. 2 shows 88 genes that were upregulated and 30 genes were downregulated by at least two-fold in urine sediment of kidney transplant patients collected at the time of acute rejection (n=17) when compared to urine sediment collected from transplant recipients without rejection (n=29).

To confirm these results in a larger set of subjects we obtained additional urine samples collected as part of the CTOT-10, CTOT-15 and CTOT-16 studies to bring our total sample set to 29 control and 17 acute rejection samples. The NanoString analyses indicated 88 genes upregulated by at least 2-fold during rejection vs. controls with 9 upregulated by at least 5-fold and 30 genes down-regulated by at least two-fold during acute rejection with 11 of those down-regulated by at least 5-fold (FIG. 2).

Figure 3:
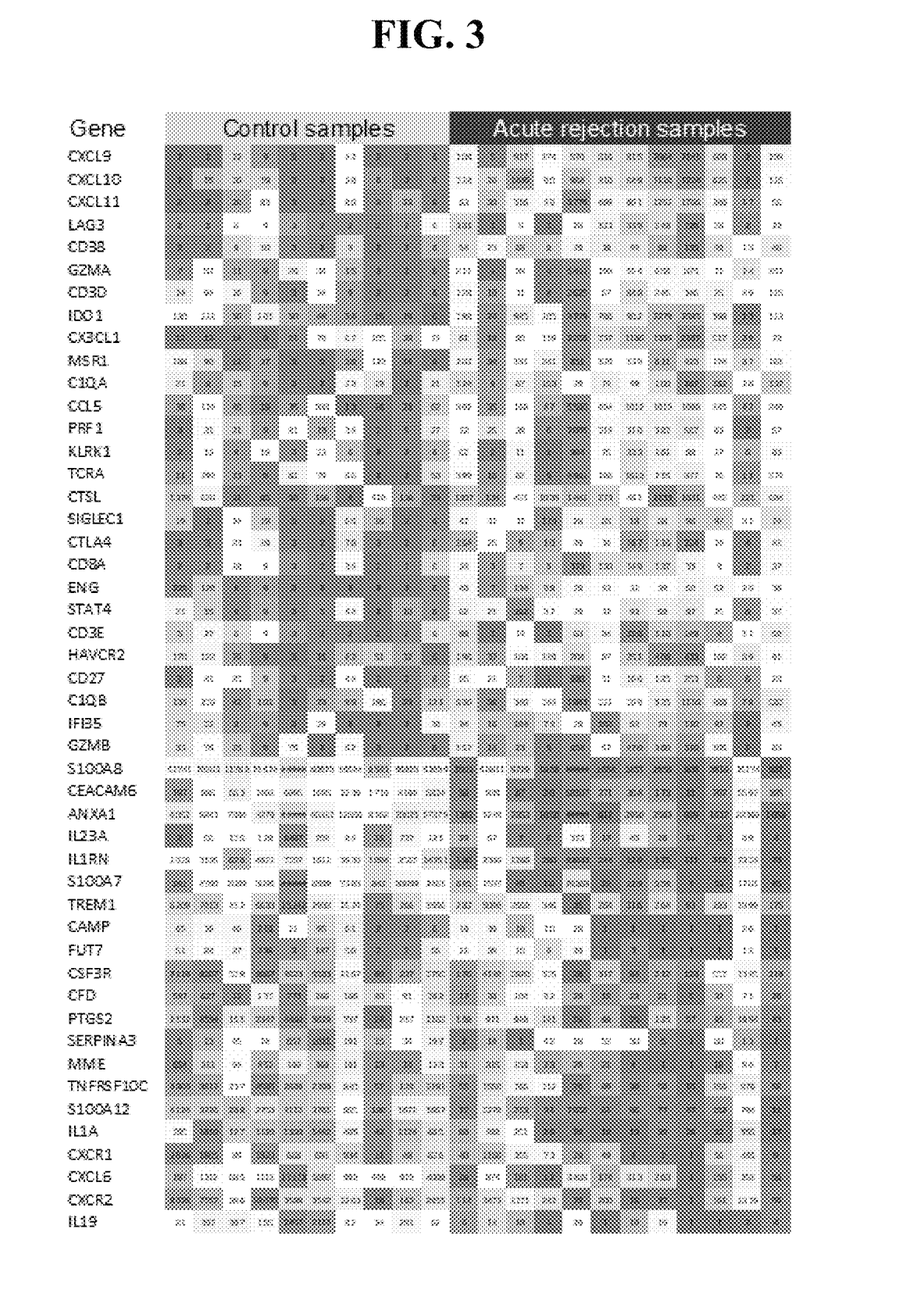
FIG. 3 shows the gene expression in the urine sediment at the time of acute rejection in 12 subjects with biopsy-proven acute rejection and 10 control subjects. Twenty-seven genes are upregulated by at least 5-fold in rejectors compared to controls and 21 genes are down-regulated by at least 5-fold.
Figure 4A:
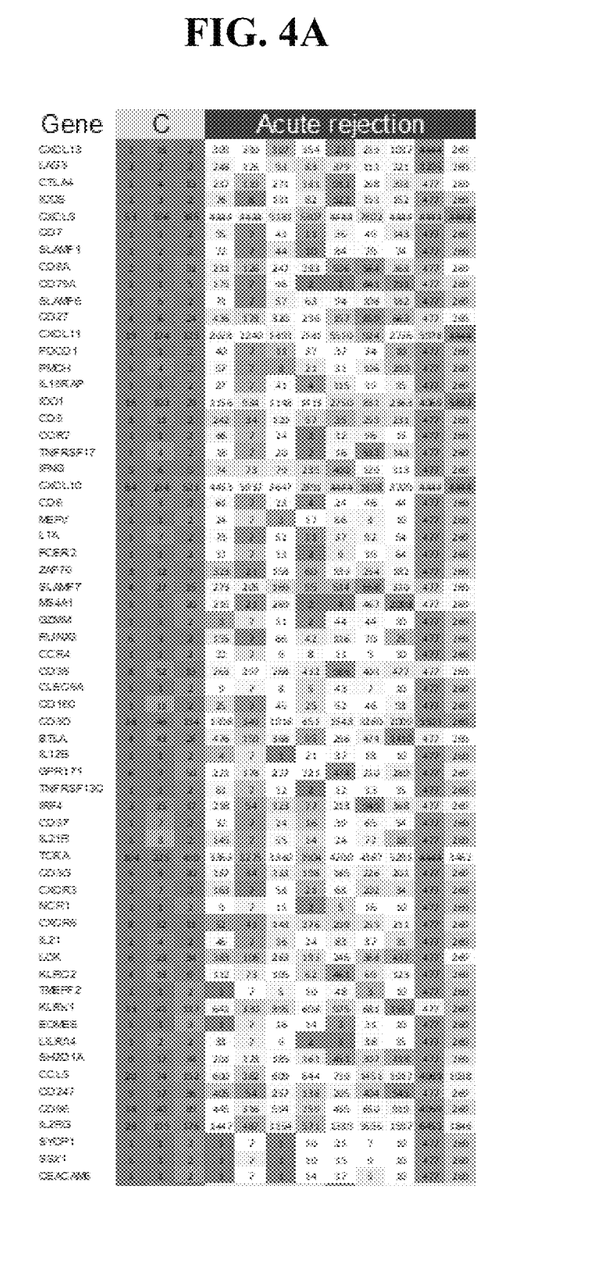
Figure 5:
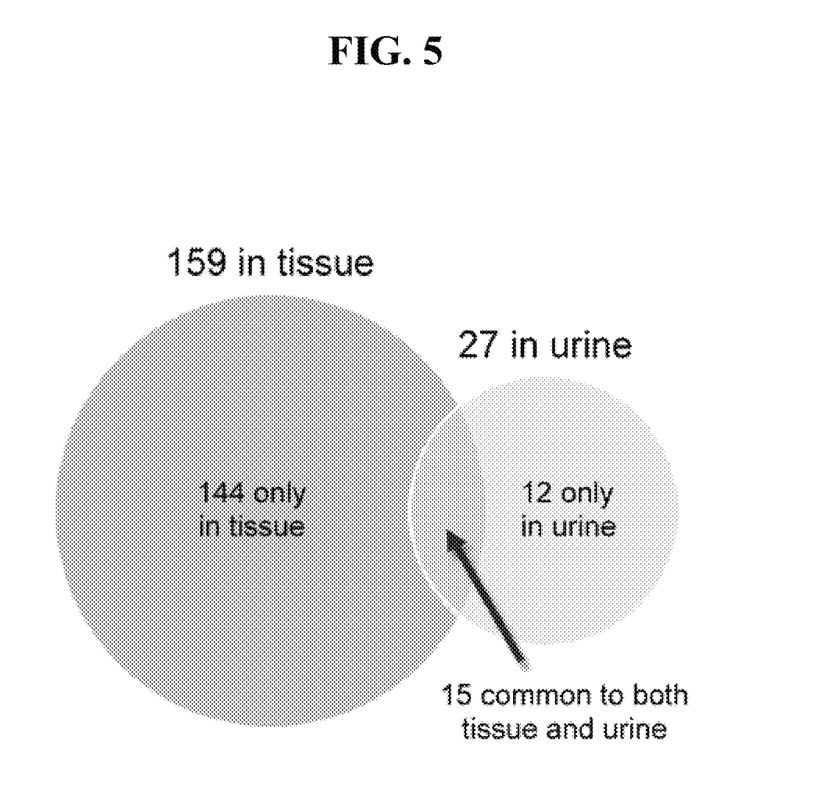
FIG. 5 shows genes upregulated by at least 5-fold at the time of acute rejection in the urine sediment and graft tissue of kidney graft recipients.

Next, we performed a comparison of gene expression patterns in RNA isolated from urine vs. biopsy during acute kidney graft rejection using urine RNA from 12 samples obtained during biopsy proven rejection and 10 samples from control/non-rejecting grafts and RNA from kidney graft biopsies from 9 samples obtained during acute rejection and 3 obtained from grafts without rejection. In the urine RNA samples 27 genes were upregulated by 5-fold or greater at the time of clinically diagnosed rejection and 21 genes were down-regulated (FIG. 3). For the graft biopsy RNA samples, 159 genes were upregulated by 5-fold or greater at the time of rejection with no genes down-regulated (FIGS. 4A-4C). Of the genes upregulated 5-fold or greater in urine and biopsy tissue during ongoing acute rejection (FIG. 5), 15 were common to both urine and graft tissue (Table 2) and 144 were unique to graft tissue and 12 were unique to urine (Table 3).

TABLE 2

| Gene | Control samples (C) | Rejection samples (AR) | Fold-change AR/C | P value |
| --- | --- | --- | --- | --- |
| expression in urine | | | | |
| CXCL9 | 5 | 269 | 52.8 | 4E−05 |
| CXCL10 | 8 | 261 | 34.1 | 6E−05 |
| CXCL11 | 10 | 264 | 26.4 | 7E−05 |
| LAG3 | 3 | 35 | 10.6 | 0.004 |
| CD38 | 4 | 41 | 10.2 | 5E−07 |
| CD3D | 11 | 100 | 9.3 | 0.007 |
| IDO1 | 45 | 408 | 9.1 | 0.004 |
| CCL5 | 44 | 308 | 7.0 | 0.004 |
| PRF1 | 13 | 90 | 6.9 | 0.012 |
| KLRK1 | 6 | 39 | 6.8 | 0.01 |
| TCRA | 27 | 185 | 6.8 | 0.04 |
| CTLA4 | 7 | 40 | 5.9 | 0.002 |
| CD8A | 5 | 29 | 5.9 | 0.008 |
| STAT4 | 8 | 46 | 5.7 | 0.001 |
| CD27 | 7 | 37 | 5.3 | 0.03 |
| expression in tissue | | | | |
| CXCL9 | 230 | 17,242 | 75.1 | 0.02 |
| CXCL10 | 214 | 6,152 | 28.8 | 0.02 |
| CXCL11 | 75 | 3,059 | 40.9 | 0.02 |
| LAG3 | 2 | 208 | 109.0 | 6E−08 |
| CD38 | 18 | 392 | 21.9 | 0.02 |
| CD3D | 50 | 1,078 | 21.5 | 0.02 |
| IDO1 | 51 | 1,827 | 36.1 | 0.01 |
| CCL5 | 60 | 904 | 15.0 | 0.03 |
| PRF1 | 32 | 420 | 13.2 | 0.02 |
| KLRK1 | 39 | 628 | 16.0 | 0.04 |
| TCRA | 225 | 4,026 | 17.9 | 0.006 |
| CTLA4 | 4 | 296 | 78.1 | 0.02 |
| CD8A | 6 | 311 | 48.5 | 0.04 |
| STAT4 | 31 | 203 | 6.6 | 0.01 |
| CD27 | 8 | 353 | 41.5 | 0.01 |

TABLE 3

| Gene | Control samples (C) | Rejection samples (AR) | Fold-change AR/C | P value |
| --- | --- | --- | --- | --- |
| C1QA | 9 | 77 | 8.1 | 0.00004 |
| C1QB | 71 | 363 | 6.1 | 0.005 |
| C1R | 3 | 21 | 8.0 | 0.001 |
| CD3E | 5 | 26 | 5.6 | 0.01 |
| CTSL | 109 | 665 | 6.1 | 0.02 |
| CX3CL1 | 32 | 270 | 8.3 | 0.002 |
| GZMA | 12 | 116 | 9.9 | 0.01 |
| HAVCR2 | 27 | 144 | 5.3 | 0.004 |
| IFI35 | 9 | 48 | 5.1 | 0.01 |
| MSR1 | 25 | 203 | 6.2 | 0.002 |
| SIGLEC1 | 9 | 56 | 6.1 | 0.001 |
| ENG | 8 | 44 | 6.8 | 0.02 |

Figure 6:
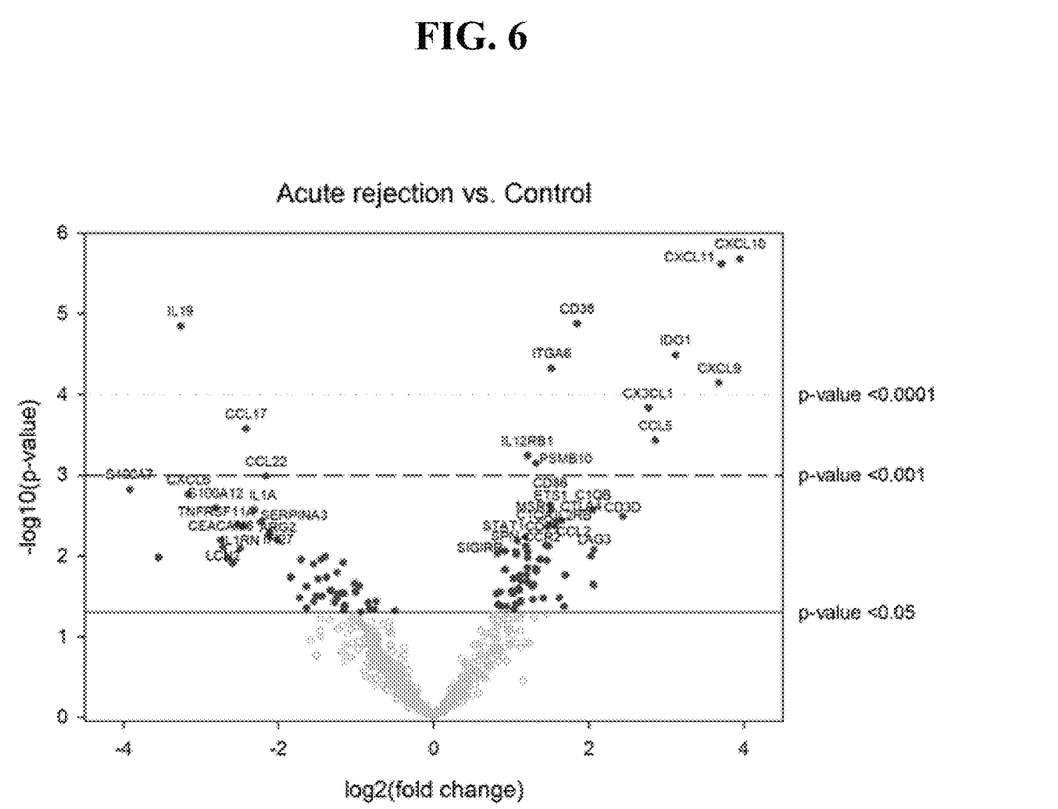
FIG. 6 shows a volcano plot illustrating differential gene expression in urine sediment RNA from subjects with acute rejection compared with control subjects.

Next, we took 29 of the urine RNA samples obtained from control/no clinical rejection recipients and 17 samples from recipients at the time of ongoing rejection. The gene expression profiles were once again analyzed by NanoString to obtain the volcano plot shown in FIG. 6 indicating the mRNA from genes upregulated during rejection vs. controls on the right side of the plot and those down-regulated on the left side of the plot.

Figure 7:
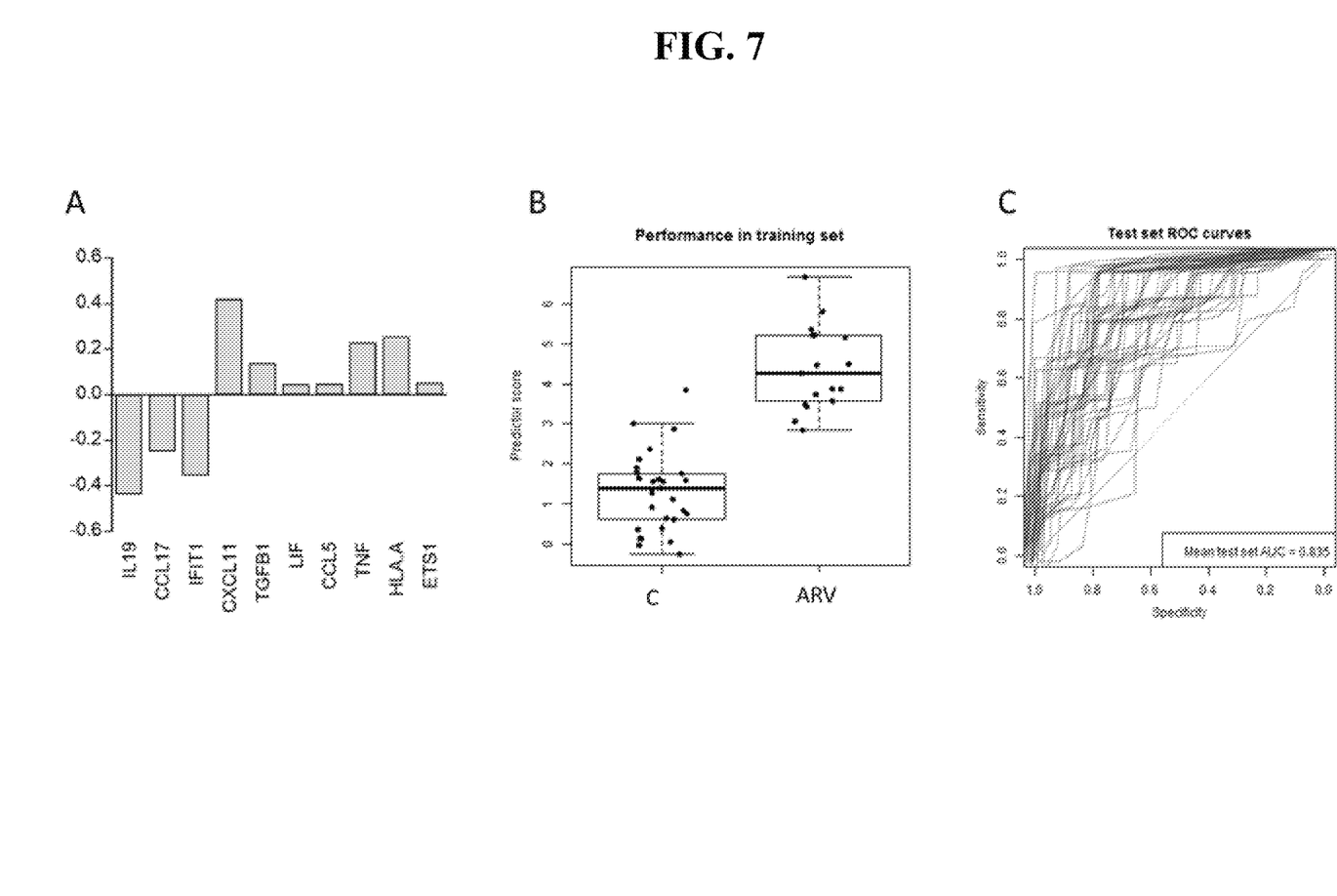
FIG. 7 shows a gene signature of acute rejection in urine. Using the elastic net, a penalized regression method that applies both the lasso and ridge penalties, we determined the 10 genes that best distinguish urine RNA samples from subjects with and without acute rejection. A) Signature genes and weights in final algorithm; B) performance of signature in training set samples; C) ROC curves and mean AUC from split-sample cross-validation.

Using the elastic net, a penalized regression method that applies both the lasso and ridge penalties, we derived a set of 10 genes for the urine RNA signature of ongoing rejection (FIG. 7). The performance of this training set indicated an excellent separation from the control RNA samples and the area under the curve (AUC) of receiver operating characteristic (ROC) curve analysis was >84%.

Figure 8:
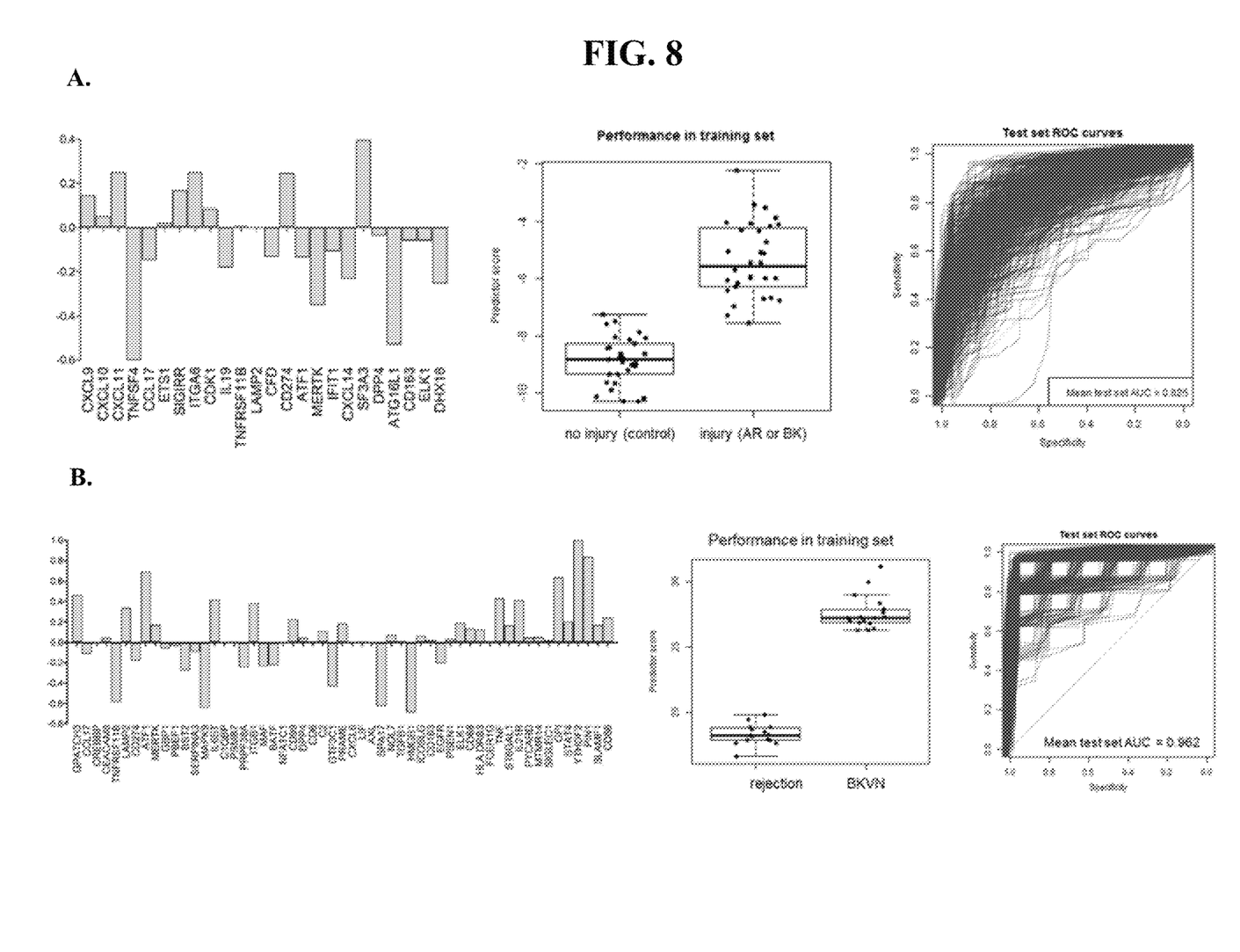
FIG. 8 Panel A shows an exemplary 24 gene signature that distinguishes injury from non-injury with an AUC of 0.825.

It can be important to distinguish immune mediated graft rejection from other causes of graft inflammation caused by infectious and other insults. We obtained urine RNA from 15 kidney transplant recipients with BK virus nephropathy and without clinical evidence of kidney graft rejection and the gene expression in these samples were compared to the 17 RNA samples from patients with ongoing rejection by NanoString. Importantly, when compared with control samples, the most significantly upregulated genes at the time of acute rejection were the same as those most upregulated during BK virus nephropathy (CXCL9, CXCL10, CXCL11, CX3CL1 and IDO1). Using the elastic net, we developed a set of 55 genes that when measured together can distinguish transplant recipients experiencing acute rejection from transplant recipients with BK virus nephropathy (AUC>96%; 95% confidence interval 0.78-0.99 by ROC curve analysis) (FIG. 8).

Figure 9:
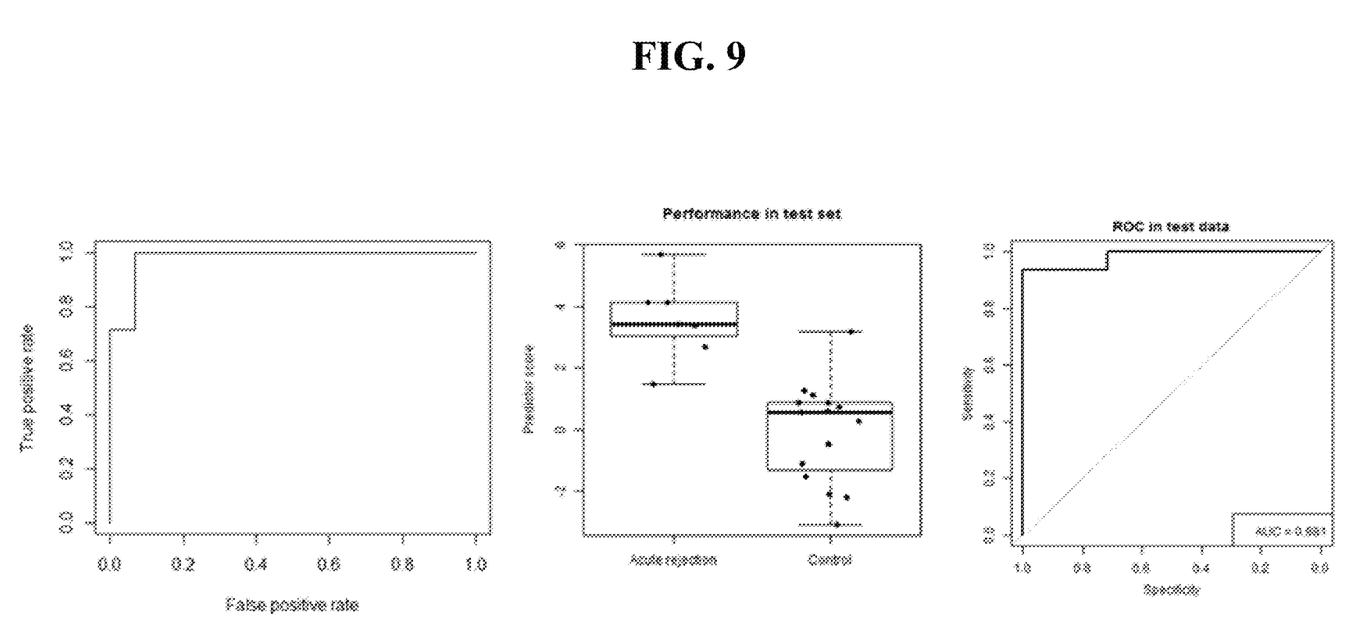
FIG. 9 shows a validation of the 10 gene acute rejection signature in a separate set of samples. The left graph shows true positive rate vs. false positive rate; the center graph shows acute rejection vs. control; and the right graph shows ROC in test data.

Finally, we obtained frozen urine sediment samples that had been collected during the CTOT-08 trial. We chose 7 ARV visits with biopsy-diagnosed T cell mediated kidney graft rejection and 15 control/no clinical rejection samples and tested the gene expression profiles and the ability of the training set of 10 genes to detect the presence vs. absence of rejection. The 10 gene test had a high True Positive and low False Positive rate (FIG. 9), a high predictor score in distinguishing acute rejection from no rejection, and the area under the curve (AUC) of receiver operating characteristic (ROC) curve analysis was >98%. Overall these results validate the 10 gene test set for the ability to detect clinically diagnosed T cell mediated rejection and support the use of this approach as a noninvasive diagnostic in kidney transplant patients.

REFERENCES

1. Keslar et al., Am. J. Transplant, 13:1891-1897, 2013.
2. Hricik et al., Am. J. Transplant, 13:2634-2644, 2013.
3. Suthanthiran et al., N. Engl. J. Med., 369:20-31, 2013.
4. Hricik et al., J. Am. Soc. Nephrol., 26:3114-3122, 2015.
5. WO2015200873
6. WO2013173493.

All publications and patents mentioned in the specification and/or listed below are herein incorporated by reference. Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope described herein.

We claim:

1. A method of detecting first and second sets of RNA markers in a urine sample and providing treatment comprising:
    a) obtaining a urine sample from a subject having a tissue or organ graft, wherein said urine sample is obtained when said subject is taking a first immunosuppressant;
    b) detecting a first set of RNA markers and a second set of RNA markers in said urine sample,
    wherein said first set of RNA markers comprises: CEACAM8, YTHDF2, and PIN1, and
    wherein said second set of RNA markers comprises: HMGB1, MAPK9, and SPA17;
    c) detecting an upregulated level of said first set of RNA markers in said urine sample, wherein each of said first set of RNA markers is upregulated when an increased expression level is detected compared to control urine samples,
    d) detecting a downregulated level of said second set of RNA markers in said urine sample, wherein each of said second set of RNA markers is downregulated when a decreased expression level is detected compared to control urine samples, and
    e) treating said subject with a second immunosuppressant that is different from said first immunosuppressant.

2. The method of claim 1, wherein said organ or tissue graft comprises a kidney or kidney tissue graft.

3. The method of claim 1, wherein said first set of RNA markers further comprises: GPI, ATF1, and GPATCH3, and said second set of RNA markers further comprises: TNFRSF11B, GTF3C1, and BST2.

4. The method of claim 3, wherein said first set of RNA markers further comprises: C2, CD68, and CD86, and said second set of RNA markers further comprises: BATF, CCL17, and CD274.

5. The method of claim 4, wherein said first set of RNA markers further comprises: CD99, ELK1, HLA.DRB3, and IL21R, and said second set of RNA markers further comprises: EGFR, and GBP1.

6. The method of claim 5, wherein said first set of RNA markers further comprises: IL6ST, ITGB1, LAMP2, and LIF, and said second set of RNA markers further comprises: MAF, and NLRC5.

7. The method of claim 6, wherein said first set of RNA markers further comprises: MERTK, NFATC1, and PRAME, and said second set of RNA markers further comprises: PBEF1, and PRPF38A.

8. The method of claim 7, wherein said first set of RNA markers further comprises: SLAMF1, ST6GAL1, STAT4, and TNF, and said second set of RNA markers further comprises: SERPINA3.

* * * * *